United States Patent [19]

Hörrmann

[11] 4,239,756
[45] Dec. 16, 1980

[54] FATTY ALDEHYDES IN THE THERAPY OF ARTERIOSCLEROSIS

[76] Inventor: Wilhelm Hörrmann, Staltacherstr. 34, D 8121 Iffeldorf, Obb, Fed. Rep. of Germany

[21] Appl. No.: 908,365

[22] Filed: May 22, 1978

Related U.S. Application Data

[60] Division of Ser. No. 787,902, Mar. 15, 1977, abandoned, which is a continuation-in-part of Ser. No. 682,309, May 3, 1976, abandoned, which is a continuation-in-part of Ser. No. 600,375, Jul. 30, 1975, abandoned, which is a continuation-in-part of Ser. No. 450,458, Mar. 12, 1974, abandoned, which is a continuation-in-part of Ser. No. 274,754, Jul. 24, 1972, abandoned, which is a continuation-in-part of Ser. No. 805,934, Feb. 12, 1969, abandoned, which is a continuation-in-part of Ser. No. 634,884, May 1, 1967, abandoned, which is a continuation-in-part of Ser. No. 412,862, Nov. 20, 1964, abandoned, which is a continuation-in-part of Ser. No. 211,827, Jul. 24, 1962, abandoned, which is a continuation-in-part of Ser. No. 824,798, Jul. 3, 1959, abandoned.

[51] Int. Cl.$^2$ .................. A61K 31/11; A61K 31/335; A61K 31/575

[52] U.S. Cl. .................................... 424/238; 424/278; 424/333

[58] Field of Search ................................ 424/333, 238

[56] References Cited

PUBLICATIONS

Chem. Abst. (1), 49–5299$e^f$+5289$f$ (1955).
Chem. Abst. (2), 43–1580i (1949).
Chem. Abst. (3), 31–1506$^7$ (1937).
Chem. Abst. (4), 40–1449$^9$+5697$^7$ (1949).

*Primary Examiner*—Stanley J. Friedman

[57] ABSTRACT

This application relates to the administering of fatty aldehydes to arteriosclerotic patients for therapeutic purposes.

1 Claim, No Drawings

FATTY ALDEHYDES IN THE THERAPY OF ARTERIOSCLEROSIS

The application is a division of Ser. No. 787,902, filed Mar. 15, 1977, which is a continuation-in-part of Ser. No. 682,309, filed May 3, 1976, which is a continuation-in-part of Ser. No. 600,375, filed July 30, 1975, which is a continuation-in-part of Ser. No. 450,458, filed Mar. 12, 1974, which is a continuation-in-part of Ser. No. 274,754, July 24, 1972, which is a continuation-in-part of Ser. No. 805,934, Feb. 12, 1969, which is a continuation-in-part of Ser. No. 634,884, filed May 1, 1967, which is a continuation-in-part of Ser. No. 412,862, Nov. 20, 1964, which is a continuation-in-part of Ser. No. 211,827, July 24, 1962 which is a continuation-in-part of Ser. No. 824,798, filed July 3, 1959, all abandoned.

Introduction

This application relates to arteriosclerosis a widespread and formidable disease causing death and invalidity of many hundreds of thousands of people all over the world. It also relates to the allied conditions and complications of arteriosclerosis to which belong ischemia and infarction of heart and brain, ischemia and gangrene of extremities, aneurysmas and others.

While arteriosclerosis means increase of connective (and Muscular) tissue in the arteries, the synonymous expression atherosclerosis is indicating the deposition of fatty substances therein. However a person may die of arteriosclerosis without having sclerosis or atheromatosis at all in his blood vessels. This was already known to U.S. Army pathologists in the Korean war, who observed the so called initial edema of the intima. As the primary and essential alterations of arteriosclerosis are to be considered the abnormal formation of fissures and hollow spaces in the arteries tunica intima, which are blown or widened up by edema in the acute, by deposition of fatty masses, especially cholesterol, in the more chronic cases. Sclerosis, calcinosis and even ulceration may follow. At any stage the intima process may hurt the endothelial lining, whereupon thrombosis will follow with all its catastrophic consequences.

The basic concept of this invention is this: that the primary formation of fissures and hollow spaces in the intima is caused by a lack in the arterial tissue of certain special lipids, containing characteristically fatty aldehydes, which are also called plasmalogens.

This was affirmed in a most impressive way by the findings of the U.S. scientists Miller, Anderson and Piantadosi (Journal of Gerontology Vol. 19, No. 4, October 1964) which sponsored by the U.S. life insurance Medical Research Fund, the National Science Foundation and the University of North Carolina confirmed similar observations of the German scientists Buddecke and Andresen. Miller, Anderson and Piantadosi found comparing normal and atherosclerotic aortic tissue, that in case of atherosclerosis the content of the tissue in plasmalogens and therewith in fatty aldehydes containing lipids is definitely and significantly reduced.

Therefore it is indicated to do here, what is done in many other fields of medicine, and what is called there a substitution therapy: namely to administer to the arteriosclerotic patient fatty aldehydes in order to compensate for the lack he has thereof.

Description

It has been found that arteriosclerosis is associated with disorders in the body of one or more of the geometric or optical isomers of the following compounds:
6-n-dodecenoic aldehyde 2 isomers
8-n-hexadecenoic-aldehyde 2 isomers
6,12-n-octadecadienoic-aldehyde 4 isomers
8,16-n-tetracosadienoic-2-hydroxy-aldehyde 8 isomers

Derivatives of the Aldehydes

Aldehydes occur per se and in different modifications:
in enolic form
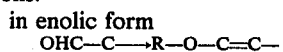
OHC—C——→R—O—C=C— wherein R is H or C
in acetalic form

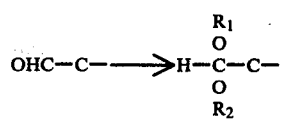

wherein $R_1$ and $R_2$ are identical or different.

Typical examples are the ethers of ethanol glycol, glycerol and the esters of acetic acid, oxalic acid and which form noncyclic or cyclic structures

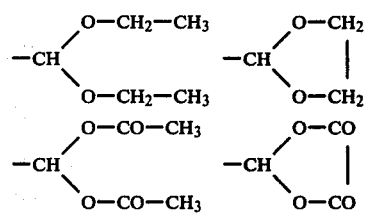

Important pharmaceutical examples for fatty aldehydes are the ethers of the aldehydes with physiologic acids of bile, namely glyco- and tauro cholic, desoxycholic, lithocholic acids, or glycerol.

HOW TO MAKE THE INVENTION (One of the many syntheses known to the art) for this type of compounds Preparation of cis and trans 6 dodecenal-diaethylacetal

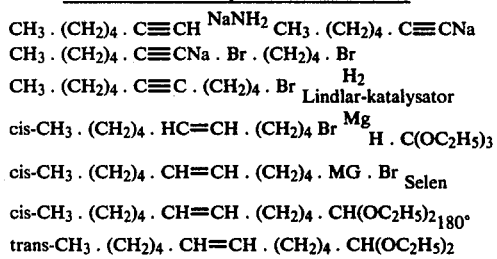

Preparation of cis and trans 8 hexadecenal-diaethylacetal

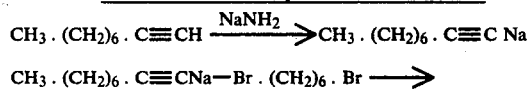

-continued
Preparation of cis and trans 8 hexadecenal-diaethylacetal $CH_3 . (CH_2)_6 . C\equiv C . (CH_2)_6 . Br \xrightarrow[\text{Lindlar-Katalysator}]{H_2}$ cis-$CH_3 . (CH_2)_6 . CH=CH . (CH_2)_6 Br \xrightarrow{Mg}$ cis-$CH_3 . (CH_2)_6 . CH=CH . (CH_2)_6 . MgBr$ cis-$CH_3 . (CH_2)_6 . CH=CH . (CH_2)_6 . MgBr \xrightarrow{H . C(OC_2H_5)_3}$ cis-$CH_3 . (CH_2)_6 . CH=CH . (CH_2)_6 . CH(OC_2H_5)_2 \xrightarrow[180°]{Selen}$ trans-$CH_3 . (CH_2)_6 . CH=CH . (CH_2)_6 . CH(OC_2H_5)_2$

$HO . (CH_2)_4 . Br + 2,3$ dihydropyran $\xrightarrow{H^\bullet}$

Preparation of pyranacetal-1-butan-4-natriumacetylid cis and trans 1,10 dibrom-dec-5-en 5  $PY . O . (CH_2)_4 . Br + Na C\equiv CH \xrightarrow{NH_3 \text{ liquid}}$ $PY . O . (CH_2)_4 . C\equiv CH \xrightarrow{Na} PY . O . (CH_2)_4 . C\equiv CNa$ $PY . O . (CH_2)_4 . C\equiv CNa + Br . (CH_2)_4 . Br \longrightarrow$ 10  $PY . O . (CH_2)_4 . C\equiv C . (CH_2)_4 . Br \xrightarrow{\text{Lindlar Katalysator}}$ $PY . O . (CH_2)_4 . CH=CH . (CH_2)_4 . Br \xrightarrow{HBr}$
cis $Br . (CH_2)_4 . CH=CH . (CH_2)_4 . Br \longrightarrow$
cis 15  $Br . (CH_2)_4 . CH=CH . (CH_2)_4 . Br$
trans

Preparation of cis trans and trans trans and cis cis 6, 12 octadecdienal-diaethylacetal $CH_3 . (CH_2)_4 . C\equiv CNa + Br . (CH_2)_4 . CH=CH . (CH_2)_4 . Br \longrightarrow$
trans
(if cis to cis cis leading)

$CH_3 . (CH_2)_4 . C\equiv C . (CH_2)_4 . CH=CH . (CH_2)_4 . Br \xrightarrow{\text{Lindlar Katalysator}}$
trans $CH_3 . (CH_2)_4 . CH=CH . (CH_2)_4 . CH=CH . (CH_2)_4 . Br$ $CH_3 . (CH_2)_4 . CH=CH . (CH_2)_4 . CH=CH . (CH_2)_4 . Br \xrightarrow{Se}$
cis                          trans $CH_3 . (CH_2)_4 . CH=CH (CH_2)_4 . CH=CH . (CH_2)_4 . Br$
trans                        trans $CH_3 . (CH_2)_4 . CH=CH . (CH_2)_4 . CH=CH . (CH_2)_4 . Br \xrightarrow{Mg}$
cis/trans                    trans $CH_3 . (CH_2)_4 . CH=CH . (CH_2)_4 . CH=CH . (CH_2)_4 . Mg Br \xrightarrow{HC(OC_2H_5)_3}$
cis/trans                    trans $CH_3 . (CH_2)_4 . CH=CH . (CH_2)_4 . CH=CH . (CH_2)_4 . CH(OC_2H_5)_2$ $CH_3 . (CH_2)_4 . CH=CH . (CH_2)_4 . CH=CH . (CH_2)_4 Br \xrightarrow{Mg} \xrightarrow{HC(OC_2H_5)_3}$
cis                          trans $CH_3 . (CH_2)_4 . CH=CH . (CH_2)_4 . CH=CH . (CH_2)_4 . CH (OC_2H_5)_2 \; S \longrightarrow$
cis                          trans $CH_3 . (CH_2)_4 CH=CH . (CH_2)_4 . CH=CH . (CH_2)_4 . CH(OC_2H_5)_2$
trans                        trans

Preparation of cis cis and trans cis and trans trans 6, 12 octadecdienal - diaethylacetal $CH_3 . (CH_2)_4 . Br + NaC\equiv CH \xrightarrow{NH_3 \text{ Liquid}}$ $CH_3 . (CH_2)_4 . C\equiv CH \xrightarrow{Na} CH_3 . (CH_2)_4 . C\equiv CNa$ $CH_3 . (CH_2)_4 . C\equiv CNa + Br . (CH_2)_4 . Br \longrightarrow$ $CH_3 . (CH_2)_4 . C\equiv C . (CH_2)_4 . Br \xrightarrow{\text{Lindlar katalysator}}$ $CH_3 . (CH_2)_4 . CH=CH . (CH_2)_4 . Br$
cis $CH_3 . (CH_2)_4 . CH=CH . (CH_2)_4 . Br + NaC\equiv C . (CH_2)_4 . O . PY$ $CH_3 . (CH_2)_4 . CH=CH . (CH_2)_4 . C\equiv C . (CH_2)_4 . O . PY \xrightarrow{\text{Lindlar Katalysator}}$
cis $CH_3 . (CH_2)_4 . CH=CH . (CH_2)_4 . CH=CH . (CH_2)_4 . O . PY \xrightarrow{H . Br}$
cis                          cis $CH_3 . (CH_2)_4 . CH=CH . (CH_2)_4 . CH=CH . (CH_2)_4 . Br \xrightarrow{Mg}$
cis                          cis -continued

Preparation of cis cis and trans cis and trans trans 6, 12 octadecdienal - diaethylacetal $CH_3 . (CH_2)_4 . \underset{cis}{CH=CH} . (CH_2)_4 . \underset{cis}{CH=CH} . (CH_2)_4 . MgBr \xrightarrow{HC(OC_2H_5)_3}$ $CH_3 . (CH_2)_4 . \underset{cis}{CH=CH} . (CH_2)_4 . \underset{cis}{CH=CH} . (CH_2)_4 . CH(OC_2H_5)_2$ $CH_3 . (CH_2)_4 . \underset{cis}{CH=CH} . (CH_2)_4 . Br \xrightarrow{Se}$ $CH_3 . (CH_2)_4 . \underset{trans}{CH=CH} . (CH_2)_4 . Br$ $CH_3 . (CH_2)_4 . \underset{trans}{CH=CH} . (CH_2)_4 . Br + NaC\equiv C . (CH_2)_4 . O\,PY$ $CH_3 . (CH_2)_4 . \underset{trans}{CH=CH} . (CH_2)_4 . C\equiv C . (CH_2)_4 . O\,PY \xrightarrow{\text{Lindlar Katalysator}}$ $CH_3 . (CH_2)_4 . \underset{trans}{CH=CH} . (CH_2)_4 . CH=CH . (CH_2)_4 . O\,PY \xrightarrow{\text{please see above}}$ $CH_3 . (CH_2)_4 . \underset{trans}{CH=CH} . (CH_2)_4 . \underset{cis}{CH=CH} . (CH_2)_4 . CH(OC_2H_5)_2 \xrightarrow{Se}$ $CH_3 . (CH_2)_4 . \underset{trans}{CH=CH} . (CH_2)_4 . \underset{trans}{CH=CH} . (CH_2)_4 . CH(OC_2H_5)_2$

Preparation of pyranacetal-1-pentan-5-natriumacetylid and cis and trans brom 1-tridec-7-en-13 pyranacetal

$HO\,(CH_2)_5 . Br + \text{2,3 dihyropyran} \xrightarrow{H^\bullet}$ $PY\,O . (CH_2)_5 . Br + Na\,C\equiv CH \xrightarrow{NH_3\,liquid}$ $PY\,O . (CH_2)_5 . C\equiv CH \xrightarrow{Na} PY\,O . (CH_2)_5 . C\equiv Na$ $PY\,O . (CH_2)_5 . C\equiv CNa + Br . (CH_2)_6\,Br \longrightarrow$ $PY\,O . (CH_2)_5 . C\equiv C . (CH_2)_6 . Br \xrightarrow{\text{Lindlar Katalysator}}$ $PY\,O . (CH_2)_5 . \underset{cis}{CH=CH} . (CH_2)_6 . Br \xrightarrow{Se}$ $PY\,O . (CH_2)_5 . \underset{trans}{CH=CH} . (CH_2)_6 . Br$

Preparation of cis cis, trans cis, and trans trans 1 brom - dicosa - 6, 14 - dien $CH_3 . (CH_2)_6 . C\equiv C\,Na + Br . (CH_2)_6 . Br \longrightarrow$ $CH_3\,(CH_2)_6 . C\equiv C . (CH_2)_6 . Br \xrightarrow{\text{Lindlar katalysator}}$ $CH_3 . (CH_2)_6 . \underset{cis}{CH=CH} . (CH_2)_6 . Br \xrightarrow{Se}$ $CH_3 . (CH_2)_6 . \underset{trans}{CH=CH} . (CH_2)_6 . Br$ $CH_3 . (CH_2)_6 . \underset{cis/trans}{CH=CH} . (CH_2)_6 . Br + Na\,C\equiv C . (CH_2)_5\,O\,PY$ $CH_3 . (CH_2)_6 . \underset{cis/trans}{CH=CH} . (CH_2)_6 . C\equiv C . (CH_2)_5 . OPY \xrightarrow{\text{Lindlar katalysator}}$ $CH_3 . (CH_2)_6 . \underset{cis/trans}{CH=CH} . (CH_2)_6 . \underset{cis}{CH=CH} . (CH_2)_5 . O\,PY \xrightarrow{H\,br}$ $CH_3 . (CH_2)_6 . \underset{cis/Trans}{CH=CH} . (CH_2)_6 . \underset{cis}{CH=CH} . (CH_2)_5\,Br$ $CH_3 . (CH_2)_6 . \underset{trans}{CH=CH} . (CH_2)_6 . \underset{cis}{CH=CH} . (CH_2)_5 . Br \xrightarrow{Se}$ $CH_3 . (CH_2)_6\,\underset{trans}{CH=CH} . (CH_2)_6 . \underset{trans}{CH=CH} . (CH_2)_5 . Br$

Preparation of cis cis, cis trans and trans trans 1-brom-docosa-6,14-dien $CH_3 . (CH_2)_6 . C\equiv C\,Na + Br\,(CH_2)_6 . \underset{cis\,or\,trans}{CH=CH} . (CH_2)_5 . O\,PY \longrightarrow$ $CH_3 . (CH_2)_6 . C\equiv C . (CH_2)_6 . \underset{cis/trans}{CH=CH} . (CH_2)_5 . O\,PY \xrightarrow{\text{Lindlar Katalysator}}$ $CH_3 . (CH_2)_6 . \underset{cis}{CH=CH} . (CH_2)_6 . \underset{cis/trans}{CH=CH} . (CH_2)_5 . O\,PY \xrightarrow{HBr}$ $CH_3 . (CH_2)_6 . \underset{cis}{CH=CH} . (CH_2)_6 . \underset{cis/trans}{CH=CH} . (CH_2)_5 . Br$ $CH_3 . (CH_2)_6 . \underset{cis}{CH=CH} . (CH_2)_6 . \underset{trans}{CH=CH} . (CH_2)_5 . Br \xrightarrow{Se}$ $CH_3 . (CH_2)_6 . \underset{trans}{CH=CH} . (CH_2)_6 . \underset{trans}{CH=CH} . (CH_2)_5 . Br$ Preparation of cis cis, cis trans, trans trans
optical α and β
8, 16 tetracosadienoic-2-hydroxy-aldehyd-
diaethylacetal

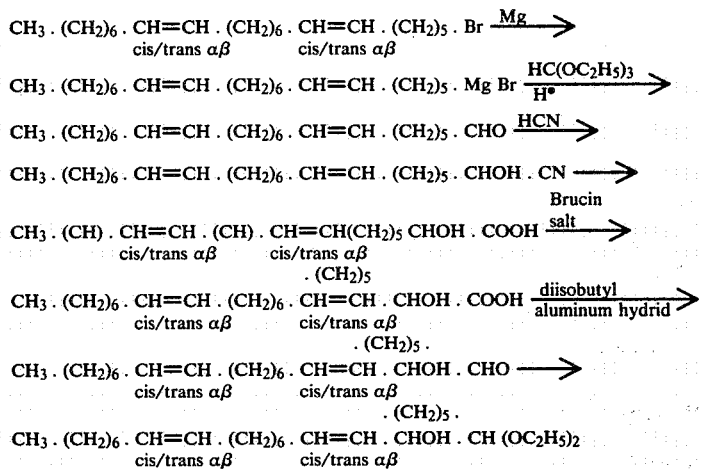

Note: In the foregoing syntheses instead of the dihalogen compounds of the type Br (CH$_2$)$_x$ Br (two halogen-atoms of the same kind) also dihalogen compounds of the type Cl (CH$_2$)$_x$.O or others (two halogen-atoms of different types) can be used.

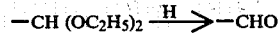

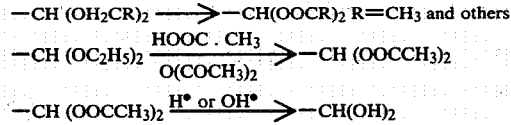

Preparation of the physilogic acids of bile (or other) ethers of the fatty aldehydes To 100 gram of taure- and/or glycocholic acid are added 0.5 gram of dried HCl. The mixture is heated with 60 gram of the respective aldehyde. The separation of the single compounds is performed by chromatography or other methods, known to the art.

It is also well known to the art that condensation of aldehydes with alcohols like glycerol leads to cyclic acetals whereby ferrum III chlorid or sulfon acids may act as catalysators. Disintegration of the acetals (with organic sulfonacids as catalyst.) and other methods result in enol-ether-type comounds of the aldehydes. All these reactions are well known to the art.

HOW TO USE THE INVENTION

It is preferred to administer the compounds in form of mixtures. That mixtures should preferably contain all isomers of the compounds which are named below. The proportion of the compounds in the mixture should preferably correspond to their molecular weight, with the exception of dodecenoic aldehyde and hexadecenoic aldehyde where the molecular weight should be doubled.

Dosage pro die 50 mg/kg—150 mg/kg or more

Dosages are general mean values, which may be raised in case of insufficient therapeutic results.

All dosages refer to the free compounds of the mixtures.

The total dosage per dag must not be given in one single dose but in several doses distributed over the day. Beeing a substitution therapy the administration must be continued over long periods of time, sometimes for months and years.

The intravenous administration of lipid substances is generally not without danger. Therefore where injection therapy seems to be absolutely indispensable the intramusculary method should be employed. The compounds preferably in their free form should be diluted in fine plant oils for pharmaceutical purposes. Proportion compounds' mixture to plant oil preferably 1 to 4 gram.

The preferred method of administering however is the peroral one, so for example as others of physiologic acids of bile or glycerol and for example in form of capsules, or emulsion.

I claim:

1. A method of treating arteriosclerosis in a patient comprising administered to said patient 50 mg/kg-150 mg/kg daily of at least one of the geometric and optical isomers of
   6-n-dodecenoic aldehyde
   8-n-hexadecenoic aldehyde
   6,12-n-octadecadienoic aldehyde or
   8,16-n-tetracosadienoic-2-hydroxy-aldehyde per se or as an ether of glycerol or physiological acids of bile, said isomer being in the form of capsule or emulsion.

* * * * *